(12) United States Patent
Avellanet (10) Patent No.: US 6,248,955 B1
(45) Date of Patent: *Jun. 19, 2001

(54) ELECTRICAL CABLES HAVING LOW RESISTANCE AND METHODS OF MAKING THE SAME

(75) Inventor: Francisco J. Avellanet, Coral Gables, FL (US)

(73) Assignee: General Science and Technology Corp, Miami, FL (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/450,879

(22) Filed: Nov. 29, 1999

Related U.S. Application Data (63) Continuation of application No. 08/843,405, filed on May 2, 1997, now Pat. No. 5,994,647.

(51) Int. Cl.$^7$ .................................................. H01B 5/08
(52) U.S. Cl. ................................. 174/128.1; 174/128.2; 174/126.1; 174/125.1
(58) Field of Search .......................... 174/128.1, 128.2, 174/126.1, 125.1; 156/51

(56) References Cited

U.S. PATENT DOCUMENTS

| H1239 | 10/1993 | Dusek ................................. 264/63 |
| 251,114 | 12/1881 | Hallidie . |
| 1,742,172 | 12/1929 | Atwood . |
| 1,888,076 | 11/1932 | Evans . |

(List continued on next page.)

FOREIGN PATENT DOCUMENTS

| 595245 | 4/1934 | (DE) . |
| 480427 | 4/1992 | (EP) . |
| 0 537 618A1 | 4/1993 | (EP) . |
| 0642 876 A1 | 8/1994 | (EP) . |
| 649636 | 4/1995 | (EP) . |
| 666086 | 8/1995 | (EP) . |
| 197692 | * 5/1923 | (GB) .............................. 174/128.1 X |
| 278233 | 10/1927 | (GB) . |

OTHER PUBLICATIONS

Suhner, How to produce efficiently flexible shafts and casings; May/Jun. 1978, Wire , pp 109–112.
W.Berg, More twists for flexible shafts couplings; Aug. 21, 1997, Machine Design, p. 152.
Fogiel, Modern Microelectronics, 1972, pp 735–737.
Kelly, A Plating Process for Ensuring Component Lead Solderability, SMT, Oct. 1997, pp 68,70.
Hesterlee, Trapwire Constructions; Wire Technology/ International, Mar. 1997, pp 51–53.
Wright, A Short Discussion of the significance of the Delta Parameter in wire drawing, Wire Journal, Oct. 1979, pp 60–61.

*Primary Examiner*—Dean A. Reichard
*Assistant Examiner*—Charlie Nguyen
(74) *Attorney, Agent, or Firm*—David P. Gordon; David S. Jacobson; Thomas A. Gallagher (57) ABSTRACT

An electrically conductive cable includes a number of conductive strands which are twined to form a wire rope. The wire rope is drawn through a die to reduce its diameter until the outer surface of the conductor is smooth and the cross section of the conductor is substantially circular. According to a presently preferred embodiment, the electrically conductive cable is successively drawn through four dies of decreasing diameter so that the overall diameter of the wire rope is reduced by at least approximately 18 percent. The resulting electrically conductive cable has the tensile strength advantage and the low resistance advantage of a solid conductor with the flexibility advantage of a wire rope cable. In addition, the smooth outer surface of the electrically conductive cable according to the invention is easily insulated with an extruded material.

19 Claims, 6 Drawing Sheets

U.S. PATENT DOCUMENTS

| | | | |
|---|---|---|---|
| 1,888,807 | 11/1932 | Rivers . | |
| 1,904,162 | 4/1933 | Milliken . | |
| 1,943,082 | 1/1934 | MacKenzie | 261/49 |
| 1,943,086 | 1/1934 | McKnight | 173/264 |
| 1,943,087 | 1/1934 | Potter | 173/264 |
| 2,071,709 | 2/1937 | Riddle | 117/16 |
| 2,135,800 | 11/1938 | Davignon | 88/52 |
| 2,154,551 | 4/1939 | Wodtke . | |
| 2,156,652 | 5/1939 | Harris | 57/145 |
| 2,396,734 | 3/1946 | Williams, Jr. . | |
| 2,427,507 | 9/1947 | Powell . | |
| 2,978,860 | 4/1961 | Campbell | 57/148 |
| 3,083,817 | 4/1963 | Campbell | 205/2 |
| 3,130,536 | 4/1964 | Peterson et al. | 57/161 |
| 3,131,469 | 5/1964 | Glaze | 29/470.5 |
| 3,195,299 | 7/1965 | Dietz | 57/149 |
| 3,234,722 | 2/1966 | Gilmore | 57/145 |
| 3,261,908 | 7/1966 | Roche et al. | 174/128 |
| 3,295,310 | 1/1967 | Beighley | 57/145 |
| 3,352,098 | 11/1967 | Gilmore | 57/147 |
| 3,383,704 | 5/1968 | Schoerner et al. | 57/145 |
| 3,395,528 | 8/1968 | Lucht et al. | 57/145 |
| 3,444,684 | 5/1969 | Schoerner et al. | 57/161 |
| 3,601,970 | 8/1971 | Roberts et al. | 57/153 |
| 3,699,768 | 10/1972 | Roberts et al. | 57/144 |
| 3,812,666 | 5/1974 | Sarracino | 57/58.52 |
| 3,813,370 | 5/1974 | Gilmore | 57/145 |
| 3,822,542 | 7/1974 | Naud et al. | 57/145 |
| 3,842,185 | 10/1974 | Raw . | |
| 3,883,278 | 5/1975 | Hass | 425/135 |
| 3,883,371 | 5/1975 | Geary | 148/32 |
| 3,900,347 | 8/1975 | Lorenzetti et al. | 148/12 B |
| 3,922,841 | 12/1975 | Katsumata et al. | 57/145 |
| 3,923,003 | 12/1975 | Carden | 118/405 |
| 3,934,446 | 1/1976 | Avitzur | 72/206 |
| 3,942,309 | 3/1976 | Cahill | 57/9 |
| 3,955,390 | 5/1976 | Geary | 72/64 |
| 3,961,514 | 6/1976 | Geary | 72/274 |
| 3,972,304 | 8/1976 | Boucher | 118/44 |
| 3,990,874 | 11/1976 | Schulman | 65/4 B |
| 4,079,510 | 3/1978 | McGrath et al. | 29/624 |
| 4,125,741 | 11/1978 | Wahl et al. | 174/120 |
| 4,133,167 | 1/1979 | Schofield | 57/12 |
| 4,173,235 | 11/1979 | Tipper | 140/82 |
| 4,201,250 | 5/1980 | Walling et al. | 141/250 |
| 4,212,151 | 7/1980 | Schauffele et al. | 57/9 |
| 4,311,001 | 1/1982 | Glushko et al. | 57/215 |
| 4,328,662 | 5/1982 | Bretegnier et al. | 57/58.61 |
| 4,330,956 | 5/1982 | McCarthy | 43/4 |
| 4,349,694 | 9/1982 | Vives . | |
| 4,352,697 | 10/1982 | Adams et al. | 148/2 |
| 4,354,880 | 10/1982 | Adams et al. | 148/2 |
| 4,406,058 | 9/1983 | Dixon | 29/809 |
| 4,456,491 | 6/1984 | Adams et al. | 148/2 |
| 4,471,527 | 9/1984 | Nishijima | 29/872 |
| 4,473,995 | 10/1984 | Gentry | 57/9 |
| 4,514,058 | 4/1985 | Walton . | |
| 4,525,598 | 6/1985 | Tsukamoto et al. | 174/128 |
| 4,529,837 | 7/1985 | Borden | 174/128 |
| 4,579,127 | 4/1986 | Haacke | 128/772 |
| 4,651,513 | 3/1987 | Dambre | 57/217 |
| 4,654,477 | 3/1987 | Isoda . | |
| 4,679,387 | 7/1987 | Weidenhaupt et al. | 57/212 |
| 4,682,607 | 7/1987 | Vaillancourt | 128/772 |
| 4,689,444 | 8/1987 | Burgess . | |
| 4,705,096 | 11/1987 | Chia | 164/476 |
| 4,731,134 | 3/1988 | Alloin et al. | 156/53 |
| 4,759,806 | 7/1988 | Dambre | 148/12 B |
| 4,763,466 | 8/1988 | Abe et al. | 57/213 |
| 4,777,324 | 10/1988 | Lee | 174/34 |
| 4,778,246 | 10/1988 | Carroll | 350/96.23 |
| 4,843,696 | 7/1989 | Gentry et al. | 29/33 F |
| 5,018,993 | 5/1991 | Durham | 439/801 |
| 5,074,140 | 12/1991 | Sanders | 72/248 |
| 5,133,121 | 7/1992 | Birbeck et al. | 29/872 |
| 5,147,662 | 9/1992 | Nishijima et al. | 425/500 |
| 5,167,399 | 12/1992 | Delomel | 254/134.3 R |
| 5,190,546 | 3/1993 | Jervis | 606/78 |
| 5,211,772 | 5/1993 | Ashida et al. | 148/336 |
| 5,215,246 | 6/1993 | Thompson et al. | 228/171 |
| 5,240,520 | 8/1993 | Tarui et al. | 148/532 |
| 5,242,759 | 9/1993 | Hall | 428/610 |
| 5,260,516 | 11/1993 | Blackmore | 174/113 A |
| 5,343,934 | 9/1994 | Wilson | 164/476 |
| 5,368,661 | 11/1994 | Nakamura et al. | 148/512 |
| 5,418,333 | 5/1995 | Sanders | 174/129 |
| 5,437,748 | 8/1995 | Bhagwat et al. | 148/532 |
| 5,451,718 | 9/1995 | Dixon | 174/102 R |
| 5,486,183 | 1/1996 | Middleman et al. | 606/127 |
| 5,520,194 | 5/1996 | Miyata et al. | 128/772 |
| 5,535,612 | 7/1996 | Vijayakar | 72/43 |
| 5,588,443 | 12/1996 | Davidson | 128/772 |
| 5,597,378 | 1/1997 | Jervis | 606/78 |
| 5,616,197 | 4/1997 | Helfer et al. | 152/527 |
| 5,632,746 | 5/1997 | Middleman et al. | 606/78 |

\* cited by examiner

ELECTRICAL CABLES HAVING LOW RESISTANCE AND METHODS OF MAKING THE SAME

This application is a continuation qf U.S. Ser. No. 08/843,405, filed May 2, 1997, now U.S. Pat. No. 5,994,647 which is hereby incorporated by reference herein in its entirety.

BACKGROUND OF THE INVENTION

1. Field of the Invention

The invention relates to electrically conductive cable. More particularly, the invention relates to cables having low electrical resistance, high tensile strength, good flexibility and which are easy to insulate.

2. State of the Art

Wire is manufactured from ingots using a rolling mill and a drawing bench. The preliminary treatment of the material to be manufactured into wire is done in the rolling mill where white hot billets (square.section ingots) are rolled to round wire rod. The action of atmospheric oxygen causes a coating of mill scale to form on the hot surface of the rod which must be removed. This descaling can be done by various mechanical methods (e.g., shot-blasting) or by pickling, i.e., immersion of the wire rod in a bath of dilute sulphuric or hydrochloric acid. After pickling, the wire rod may additionally undergo a jolting treatment which dislodges the scale loosened by the acid. The remaining acid is removed by immersion of the wire rod in lime water.

Figure 1:
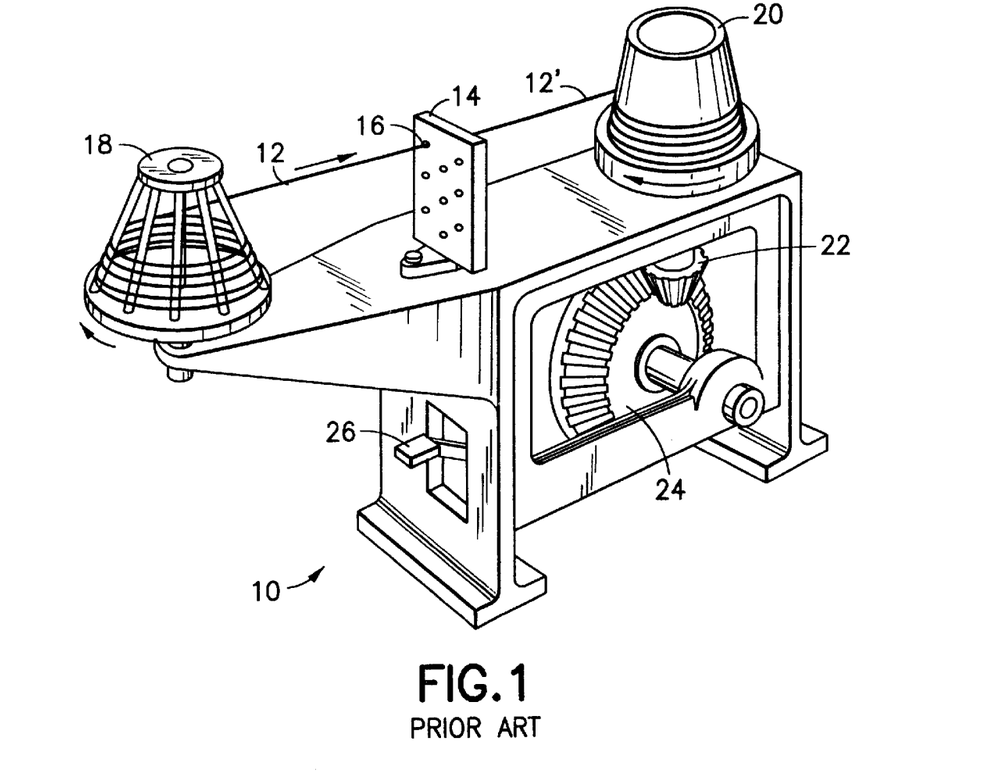
FIG. 1 is a schematic perspective view of a prior art wire drawing apparatus.

The actual process of forming the wire is called drawing and is carried out on the metal in a cold state with a drawing bench. Prior art FIG. 1 shows a simple drawing bench 10. The wire 12 is pulled through a draw plate 14 which is provided with a number of holes, e.g. 16, (dies) of various diameters. These dies have holes which taper from the diameter of the wire 12 that enters the die to the smaller diameter of the wire 12' that emerges from the die. The thick wire rod 12 is coiled on a vertical spool 18 called a swift and is pulled through the die by a rotating drum 20 mounted on a vertical shaft 22 which is driven by bevel gearing 24. The drum can be disconnected from the drive by means of a clutch 26. To pass a wire through a die, the end of the wire is sharpened to a point and threaded through the die. It is seized by a gripping device and rapidly pulled through the die. This is assisted by lubrication of-the wire. Each passage through a die reduces the diameter of the wire by a certain amount. By successively passing the wire through dies of smaller and smaller diameter, thinner and thinner wire is obtained. The dies used in the modern wire industry are precision-made tools, usually made of tungsten carbide for larger sizes or diamond for smaller sizes. The die design and fabrication is relatively complex and dies may be made of a variety of materials including single crystal natural or synthetic diamond, polycrystalline diamond or a mix of tungsten and cobalt powder mixed together and cold pressed into the carbide nib shape.

Figure 2:
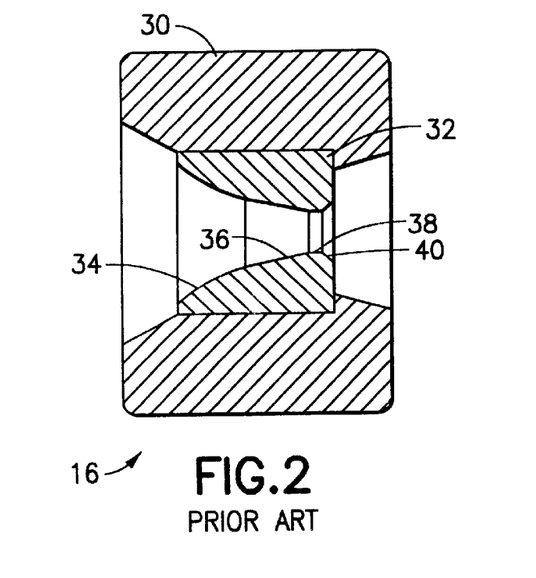
FIG. 2 is a schematic sectional view of a prior art drawing die.

A cross section of die 16 is shown in prior art FIG. 2. Generally, the dies used for drawing wire have an outer steel casing 30 and an inner nib 32 which, as mentioned above, may be made of carbide or diamond or the like. The die has a large diameter entrance 34, known as the bell, which is shaped so that wire entering the die will draw lubricant with it. The shape of the bell causes the hydrostatic pressure to increase and promotes the flow of lubricant into the die. The region 36 of the die where the actual reduction in diameter occurs is called the approach angle. In the design of dies, the approach angle is an important parameter. The region 38 following the approach angle is called the bearing region. The bearing region does not cause diametric reduction, but does produce a frictional drag on the wire. The chief function of the bearing region 38 is to permit the conical approach surface 36 to be refinished (to remove surface damage due to die wear) without changing the die exit. The last region 40 of the die is called the back relief. The back relief allows the metal wire to expand slightly as the wire leaves the die. It also minimizes the possibility of abrasion taking place if the drawing stops or if the die is out of alignment with the path of the wire.

Although wire drawing appears to be a simple metalworking process, those skilled in the art will appreciate that many different parameters affect the physical quality of the drawn wire. Among these parameters, draw stress and flow stress play an important role. If these parameters are not carefully considered, the drawn wire may have reduced tensile strength. A discussion of the practical aspects of wire drawing can be found in Wright, Roger N., "Mechanical Analysis and Die Design", Wire Journal, October 1979, the complete disclosure of which is hereby incorporated by reference herein.

The wire forming processes described above may be used to form different kinds of wires including wires which are used to conduct electricity and wires which are used as structural supports. Generally, the most important physical characteristic of a wire used to conduct electricity is its electrical resistance and the most important physical characteristic of a wire used for structural support is its tensile strength. In both types of wires, flexibility may be an important characteristic. Generally, a bundle of wire strands which are twisted together to form a cable exhibits much more flexibility than a single wire of comparable diameter. Thus, in both structural and electrical applications, where flexibility is important, stranded cables are used rather than single solid wires. Stranded cables also have the advantage that they do not kink as easily as solid wires and they can be connected to terminals by crimping. Stranded cables have some disadvantages, however. These disadvantages include lower tensile strength and higher electrical resistance than solid wires of comparable diameter. In addition, the rough outer surface presented by stranded cables makes them more difficult to insulate than solid wires. The rough outer surface of bare stranded cables also presents greater wind resistance than a smooth wire.

The electrical resistance of an electrically conductive wire is related to the chemical composition of the wire (which determines its "resistivity"), the length of the wire, and the cross sectional area of the wire. All materials have a measurable "resistivity" which defines the material as a conductor, semi-conductor, or insulator. Resistivity is indicated with the Greek letter $\rho$ (rho) and is measured in the units ohm-cm or ohm-meter (ohms per unit length). For example, insulators such as polystyrene have a resistivity on the order of $10^{20}$ ohm-cm, semiconductors such as germanium have a resistivity on the order of $10^2$ ohm-cm, drawn copper wire conductors have a resistivity of approximately $1.77 \times 10^{-6}$ ohm-cm. Resistivity is used to approximate the electrical resistance (R) of a material when it is part of an electrical circuit. The relationship between resistivity and Resistance is given in Equation 1 below, where R is resistance, $\rho$ is resistivity, L is length, and A is cross sectional area.

$$R = \rho \frac{L}{A} \qquad (1)$$

Thus, the resistance of a drawn copper wire which is 100 centimeters long and one centimeter in diameter can be expressed as shown below in Equation 2.

$$1.77 \times 10^{-6} \text{ ohm cm} A \frac{100 \text{ cm}}{.25 \pi \text{cm}^2} = 0.023 \text{ ohms} \qquad (2)$$

For convenience, when discussing conductors, resistivity can be expressed in reciprocal-form and called "conductivity". Conductivity is referred to with the Greek letter $\sigma$ (sigma) and is measured in siemens per meter or S/cm where a siemen is an ohm$^{-1}$. Thus, drawn copper wire may be said to have a conductivity of $1.77 \times 10^6$ S/cm. The conductivity (or resistivity) of a wire is a constant which is independent of cross sectional area. The resistance (or its reciprocal conductance) of a wire is a variable which is based in part on the cross sectional area of the wire.

Figure 3:
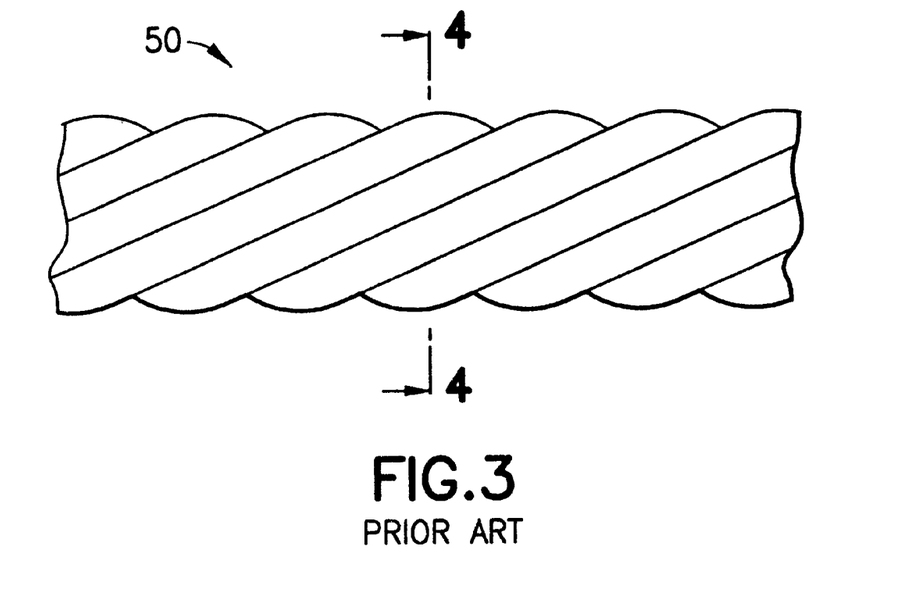
FIG. 3 is a broken schematic side elevation view of a prior art wire rope conductor.
Figure 4:
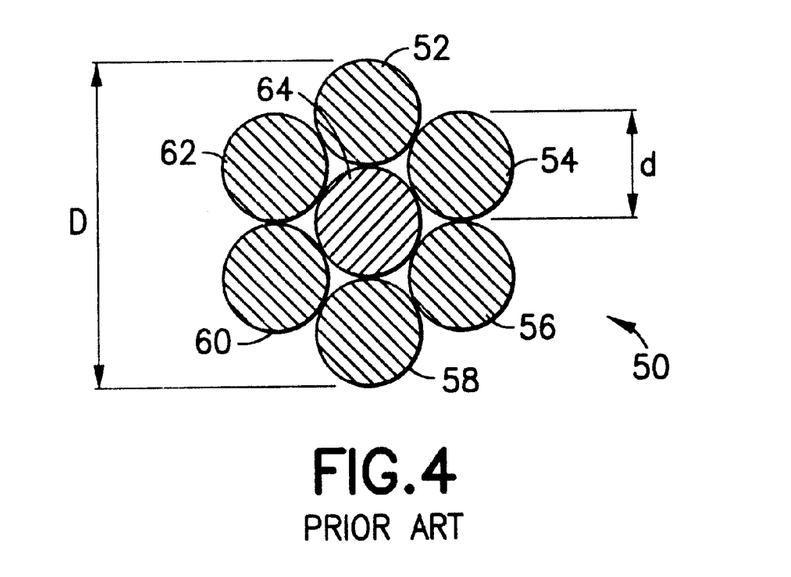
FIG. 4 is a cross-sectional view of the prior art wire rope conductor taken along line 4—4 in FIG. 3.

The twining of several strands of wire to produce a flexible cable results in a cable having an overall diameter D, but which has a smaller cross sectional area than a solid wire with the same diameter. Prior art FIGS. 3 and 4 schematically illustrate an electrical transmission cable 50. The cable 50 is shown consisting of three wire strands 52, 54, 56, each having a diameter "d". In actual practice, an electrical transmission cable may consist of many more conductive strands and one or more steel core strands which serve to enhance the tensile strength of the cable. As shown, the three strands are twined to form the conductive cable 50 having an overall diameter "D" which is approximately 2.15 d. However, the cross sectional area of the conductive cable 50, for purposes of computing the resistance (or conductance) of the cable is not as large as the cross sectional area of a solid wire having a diameter of 2.15 d. Thus, the stranded and twined cable 50 will have a higher resistance than a solid single strand of wire with the same cross sectional diameter. As mentioned above, the twining of the strands presents a rough outer surface on the cable which makes it relatively difficult to cover the cable with extruded insulation and which makes the cable more susceptible to influence by wind. These disadvantages are present in stranded cable, regardless of the number of strands.

SUMMARY OF THE INVENTION

It is therefore an object of the invention to provide an electrically conductive wire which has the advantages of a stranded twined cable but without the disadvantages of a twined cable.

It is also an object of the invention to provide an electrically conductive cable which has low electrical resistance, relatively high tensile strength, and good flexibility.

It is another object of the invention to provide a method of making an electrically conductive cable which has low electrical resistance, relatively high tensile strength, and good flexibility.

It is still another object of the invention to provide an electrically conductive cable which has a smooth surface and is easily insulated with a co-extrusion process.

In accord with these objects which will be discussed in detail below, the electrically conductive cables of the present invention include a number of conductive strands which are twined to form a wire rope. The wire rope is drawn through a die to reduce its diameter until the outer surface of the cable is substantially smooth and the cross section of the cable is substantially circular. According to a presently preferred embodiment, the conductor is successively drawn through four dies of decreasing diameter so that the overall diameter of the wire rope is reduced by 30–40%. The resulting cable has much of the flexibility advantage of a twined wire rope and much of the low resistance advantage of a solid conductor. In addition, the substantially smooth outer surface of the conductor according to the invention is easily insulated with an extruded material. The tensile strength of the drawn cable is significantly better than a wire rope of comparable diameter. Moreover, the cables according to the invention exhibit reduced parasitic reactance.

The cables according to the invention may be made of metallic strands such as copper, aluminum, stainless steel, silver, platinum, nickel, titanium, etc. The strands used to form the cable need not all be of the same material. By mixing strands of different material, the resistance, flexibility, and tensile strength of the finished cable can be carefully controlled.

Additional objects and advantages of the invention will become apparent to those skilled in the art upon reference to the detailed description taken in conjunction with the provided figures.

DETAILED DESCRIPTION OF THE PREFERRED EMBODIMENTS

Figure 5:
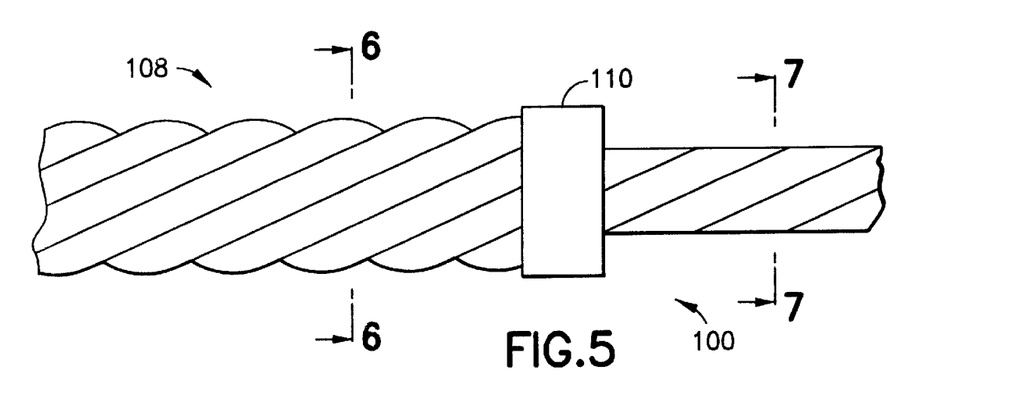
FIG. 5 is a schematic view of a wire rope being drawn through a die according to the invention.
Figure 6:
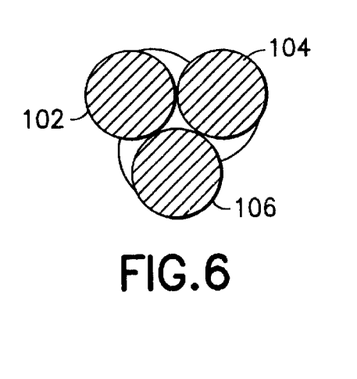
FIG. 6 is a cross-sectional view taken along line 6—6 in FIG. 5.
Figure 7:
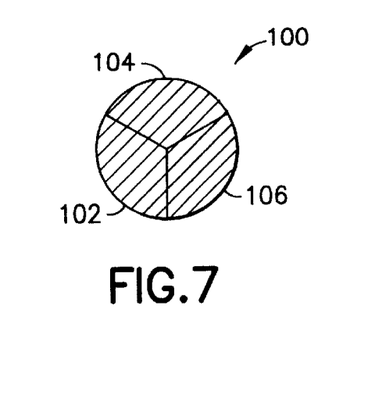
FIG. 7 is a cross-sectional view taken along line 7—7 in FIG. 5.

Referring now to FIGS. 5 through 7, an electrically conductive cable 100 according to the invention is manufactured according to the following method. Several conductive strands, e.g. strands 102, 104, 106 are twined together (i.e., such that no on one strand forms a central core) to form a wire rope 108. The wire rope 108 is pulled through a die 110 using known wire drawing methods and apparatus whereby its diameter is decreased. Preferably, the wire rope 108 is successively drawn through dies of decreasing diameter. During the drawing process, the conductors 102, 104, 106 are plastically deformed. After the successive drawing is completed, the cable assumes a substantially circular cross section as shown in FIG. 7, but maintains the flexibility advantage of a wire rope. In addition, the substantially smooth surface of the cable 100 is easily insulated with an extruded or co-extruded material. According to the presently preferred embodiment, the wire rope 108 is successively pulled through four dies of decreasing diameter. The resulting cable 100 has a diameter which is approximately 30–40% smaller than the diameter of the wire rope 108.

Although the cables according to the invention are primarily intended for use in electrical applications, cables according to the invention may be made in different sizes for different applications. The concept of the invention has been tested using three strands of stainless steel wire as explained in the Examples 1 and 2 below.

EXAMPLE 1

Figure 8:
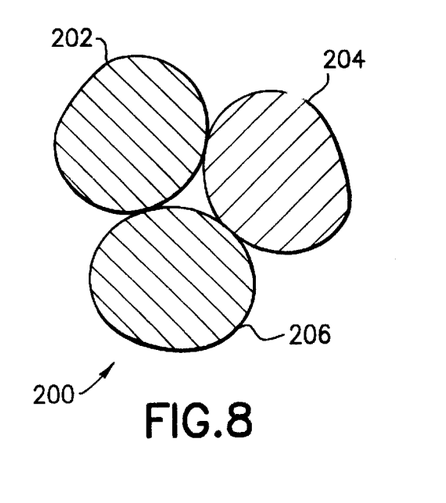
FIG. 8 is a cross-section of an exemplary embodiment of a conductor according to the invention after being drawn through a first die.
Figure 10:
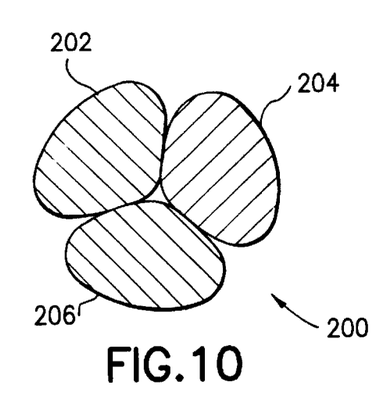
FIG. 10 is a cross-section of the conductor of FIG. 8 after being drawn through a third die.
Figure 11:
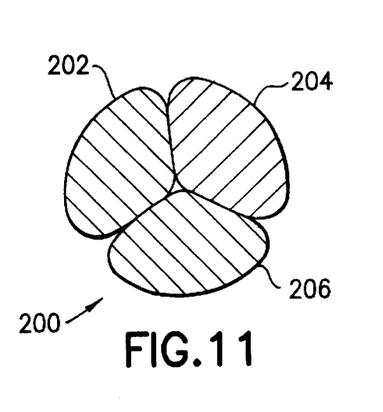
FIG. 11 is a cross-section of the conductor of FIG. 8 after being drawn through a fourth die.
Figure 12:
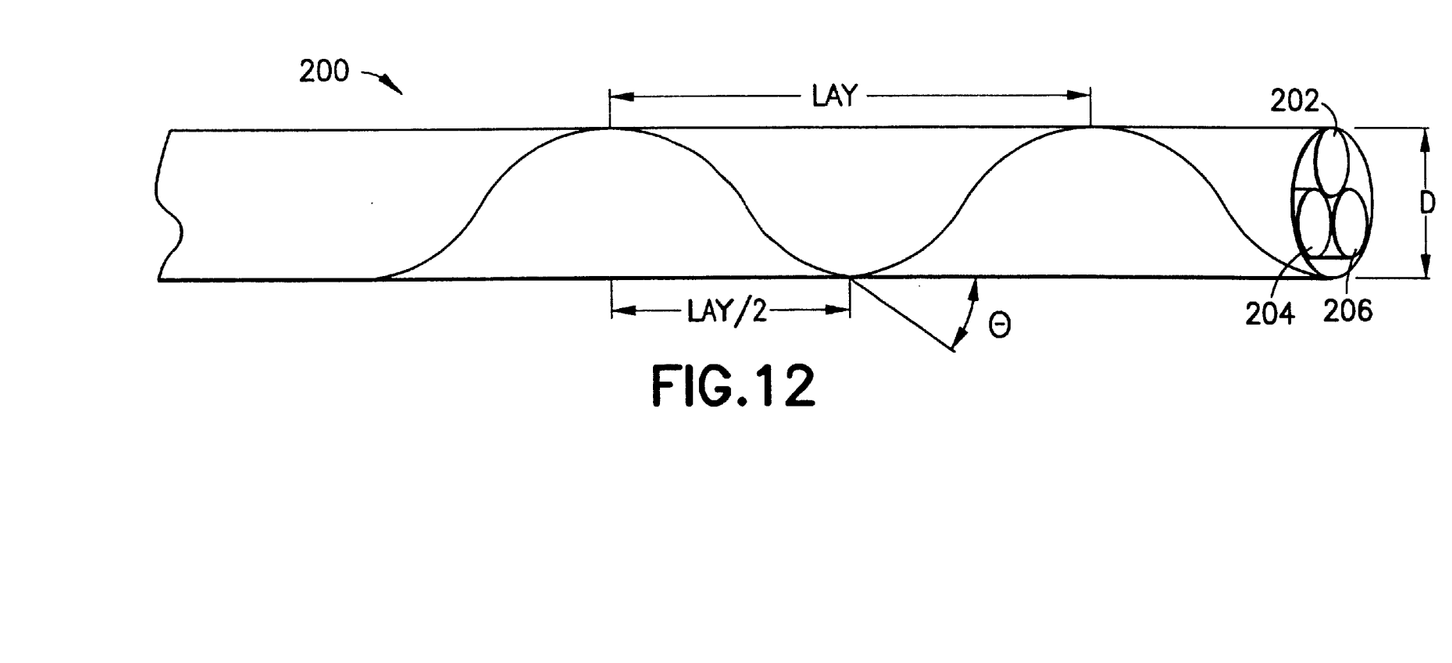
FIG. 12 is a schematic view of a conductor according to the invention.

Turning now to FIGS. 8–11, three strands of MP35N stainless steel wire 202, 204, 206 each having a diameter of approximately 0.009 inch were twisted together, as described in more detail below with reference to FIG. 12, to form a wire rope 200 having an overall diameter of approximately 0.0194 inch. The twisted wires were drawn through a first die which reduces the overall diameter of the wire rope to approximately 0.0179 inch. FIG. 8 is a micrograph at 125× magnification showing the cross section of the wire rope after being drawn through the first die.

Figure 9:
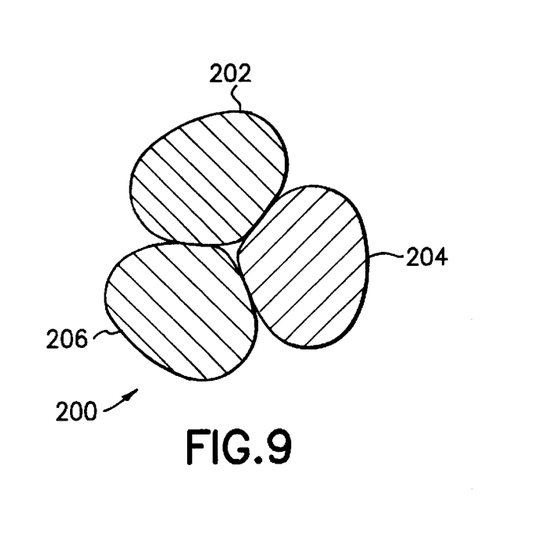
FIG. 9 is a cross-section of the conductor of FIG. 8 after being drawn through a second die.

The rope was then drawn through a second die which reduces the overall diameter of the wire rope to approximately 0.0159 inch; i.e., such that after drawings through two dies the diameter is reduced approximately 18 percent. FIG. 9 is a micrograph at 125× magnification showing the cross section of the wire rope after being drawn through the second die.

The rope was then drawn through a third die which reduces the overall diameter of the wire rope to approximately 0.0142 inch; i.e., such that after drawings through three dies the diameter is reduced approximately 26 percent. FIG. 10 is a micrograph at 125× magnification showing the cross section of the wire rope after being drawn through the third die.

The rope was then drawn through a fourth die which reduces the overall diameter of the wire rope to approximately 0.0130 inch; i.e., such that after drawings through four dies the diameter is reduced approximately 33 percent. FIG. 11 is a micrograph at 125× magnification showing the cross section of the wire rope after being drawn through the fourth die.

Comparing FIGS. 8 and 11, it will be appreciated that the drawing process results in a conductor having a substantially circular cross section With little or no wasted space in the cross sectional area of the conductor.

Those skilled in the art will appreciate that the results illustrated in FIGS. 8–11 will depend somewhat on the Lay angle of the twisted strands. Referring now to FIG. 12, the "Lay length" of strands 202, 204, 206 is the reciprocal of the number of twists per inch. The Lay angle is defined as the angle formed by a strand relative to the longitudinal axis of the conductor. The lay angle is shown in FIG. 12 as the angle θ [theta]. Those skilled in the art will appreciate that the Lay angle is related to both the Lay length and the diameter of the strand bundle. More specifically, the Lay angle $\theta = 90° - \arctan[(L/2)/D]$.

It will further be appreciated that when the diameter of the wire rope is decreased by drawing it through dies, as described above, the Lay angle of the strands will change.

According to the first example, the individual wire strands 202, 204, 206 were twisted with a Lay length of approximately 0.080 inch exhibiting a Lay angle of approximately 26°. After drawing the wire rope through four dies, as described above, the lay length was thereby increased to approximately 0.1315 inch exhibiting a Lay angle of approximately 12°.

The cable formed in Example 1 was tested for electrical resistance. The ends of a 57.5 inch long cable were attached to an ammeter and a 1 volt DC source in series and a current of 51.8 mA was measured. This corresponds to a resistance of approximately 19.3 ohms (approximately 4 ohm/ft). This was compared to a cable made from three strands of MP35-N wire which were twisted but not drawn and which had an overall diameter of approximately 0.0132 inches. The cable which was twisted but not drawn exhibited a resistance of 27.3 ohms (approximately 5.7 ohm/ft). A single strand of MP35-N wire having a diameter 0.01285 inches exhibited a resistance of 3.6 ohm/ft.

EXAMPLE 2

Three strands of 304V stainless steel wire each having a diameter of approximately 0.010 inch were twisted together to form a wire rope having an overall diameter of approximately 0.0215 inch. The strands were twisted with a Lay length of approximately 0.087 inch exhibiting a Lay angle of approximately 26°. The twisted wires were drawn successively through four dies which reduce the overall diameter of the wire rope to approximately 0.0135 inch. After drawing the wire rope through four dies, the lay length was thereby increased to approximately 0.1818 inch exhibiting a Lay angle of approximately 8°.

The cable of Example 2 exhibited an electrical resistance of approximately 3.76 ohm/ft. This compared favorably to a twisted wire rope made of three strands of 304V stainless steel wire having an overall diameter 0.0132 inches which exhibited an electrical resistance of approximately 5.21 ohm/ft. A single strand of 304V wire having a diameter of 0.0129 inches exhibited an electrical resistance of approximately 3.2 ohm/ft.

The cable of Example 2 was also tested for tensile strength exhibiting a break load of 38.6 lbs. This compared favorably to a twisted wire rope made of three strands of 304V stainless steel wire having an overall diameter 0.0132 inches which exhibited a break load of 25 lbs. A single strand of 304V wire having a diameter of 0.0135 inches exhibited a break load of 42.48 lbs.

As mentioned above, the electrical cables according to the invention exhibit high tensile strength and low electrical resistance. In addition, the electrical cables according to the invention make efficient use of space as compared to wire rope cables. Therefore, the invention may be advantageously applied to the manufacture of electrical cables of almost any size. For example, the National Electrical Code, 1996 Ed., requires that the cross sectional area of insulated cables can not occupy more than 40% of the available area of a conduit. The present invention provides cables with higher current carrying capacity but smaller diameters. This means that new cables with higher current carrying capacity can be installed in existing conduits without having to go through the expense of replacing the conduits. For example, a 4/0 stranded wire with a capacity to carry 230 amps and a cross sectional area of 0.219 in$^2$, when reduced in diameter according to the invention, will be able to fit into the conduit of 3/0 wire with a cross sectional area of 0.173 in$^2$ without having to change the conduit. In other words, the present invention will allow for the availability of cables with higher current carrying capacity within the same conduit as existing cables with less current carrying capacity. Conversely, the present invention will also allow for the development of smaller size conduits with the same current capacity as existing larger conduits. The following Examples illustrate cables of different size according to the invention.

EXAMPLE 3

Three strands of stainless steel wire each having a diameter of approximately 0.4 inch are twisted together to form a wire rope which is drawn through several dies to form a cable having an overall diameter of approximately 0.86 inch. The wire rope is continuously twisted and drawn from three spools of wire and onto a take up spool until several hundred feet of cable are obtained. The cable is useful as a replacement for electrical transmission lines.

EXAMPLE 4

Three strands of steel wire each having a diameter of approximately 0.1 inch are twisted together to form a wire rope which is drawn through several dies to form a cable having an overall diameter of approximately 0.215 inch. The wire rope is continuously twisted and drawn from three spools of wire and onto a take up spool until several hundred feet of cable are obtained. An extruded insulator is applied to the cable using known techniques. The cable is useful as a replacement for electrical distribution lines.

EXAMPLE 5

Figure 13:
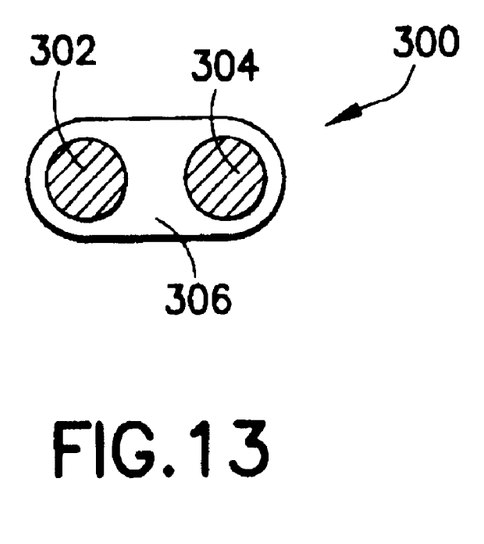
FIG. 13 is a cross-sectional view of an insulated two conductor cable according to a fifth exemplary embodiment of the invention.

Several dozen strands of copper wire are twisted together to form a wire rope which is drawn through several dies to form a cable. The wire rope is continuously twisted and drawn from several dozen spools of wire and onto a take up spool until several hundred feet of cable are obtained. Referring to FIG. 13, two spools of so formed cable 302, 304 are pulled parallel and covered with an extruded insulator 306. The insulated two conductor cable 300 is useful as a replacement for household electrical wire.

EXAMPLE 6

Five strands of aluminum wire are twisted together around a single strand of aluminum alloy wire to form a wire rope. The wire rope is continuously twisted and drawn from six spools of wire and onto a take up spool until several hundred feet of cable are obtained. The cable has enhanced strength, high flexibility, and low resistance.

There have been described and illustrated herein several embodiments of an electrical cable and a method of making it. While particular embodiments of the invention have been described, it is not intended that the invention be limited thereto, as it is intended that the invention be as broad in scope as the art will allow and that the specification be read likewise. Thus, while a particular number of strands have been disclosed, it will be appreciated that a different number of strands could be utilized. Also, while the strands have been shown with a helical twist, it will be recognized that other types of twining of strands could be used with similar results obtained. Moreover, while particular configurations have been disclosed in reference to the number of dies used and the reduction in diameter of the rope, it will be appreciated that other configurations could be used as well. It will therefore be appreciated by those skilled in the art that yet other modifications could be made to the provided invention without deviating from its spirit and scope as claimed.

What is claimed is:

1. An electrically conductive cable, comprising:
a first plurality of twined electrically conductive strands drawn through a plurality of successive dies of decreasing diameter to form a first conductive cable having a substantially circular cross section with a diameter which is at least approximately 18% smaller than an overall cross sectional diameter of said first plurality of twined electrically conductive strands, wherein no one of said first plurality of electrically conductive strands forms a central core of said cable.

2. A cable according to claim 1, wherein:
said first conductive cable is covered with an extruded insulator.

3. A cable according to claim 1, further comprising:
a second plurality of twined electrically conductive strands drawn through a die to farm a second conductive cable having a substantially circular cross section, wherein
said first conductive cable and said second conductive cable are covered with an extruded insulator to form a two conductor cable.

4. A cable according to claim 1, wherein:
said first plurality of twined electrically conductive strands are each several hundred feet in length.

5. A cable according to claim 1, wherein:
at least one of said first plurality of conductive strands is made of a different material than another of said conductive strands.

6. A cable according to claim 1, wherein:
at least a first of said first plurality of twined electrically conductive strands is formed from a different material than a second of said first plurality of twined electrically conductive strands.

7. A cable according to claim 1, wherein:
said diameter of said first conductive cable is at least approximately 24% smaller than an overall cross sectional diameter of said first plurality of twined electrically conductive strands.

8. A cable according to claim 1, wherein:
said diameter of said first conductive cable is at least approximately 30% smaller than an overall cross sectional diameter of said first plurality of twined electrically conductive strands.

9. A cable according to claim 1, wherein:
said first plurality of twined electrically conductive strands are twined with a lay angle of approximately 26 degrees.

10. A cable according to claim 1, wherein:
said first plurality of twined electrically conductive strands are twined with a lay length of approximately 0.08 to 0.09 inches.

11. A method of making an electrically conductive cable, comprising:
twining a first plurality of electrically conductive strands to form a first wire rope;
drawing the first wire rope successively through a plurality of dies of decreasing diameter to form a first electrically conductive cable having a substantially circular cross section with a diameter which is at least approximately 18% smaller than an overall cross sectional diameter of said first plurality of electrically conductive strands wherein no one of said first plurality of electrically conductive strands forms a central core of said cable.

12. A method according to claim 11, further comprising:

covering said first conductive cable with an extruded insulator.

13. A method according to claim 11, further comprising:

twining a second plurality of electrically conductive strands to form a second wire rope;

drawing the second wire rope through a die to form a second conductive cable having a substantially circular cross section;

covering the first conductive cable and the second conductive cable with an extruded insulator to form a two conductor cable.

14. A method according to claim 11, wherein:

at least one of said first plurality of conductive strands is made of a different material than another of said conductive strands.

15. A method according to claim 11, wherein:

said twining comprises twining said electrically conductive strands with a lay angle of approximately 26 degrees.

16. A method according to claim 11, wherein:

said twining comprises twining said electrically conductive strands with a lay length of approximately 0.08 to 0.09 inches.

17. A method according to claim 11, wherein:

at least a first of said first plurality of twined electrically conductive strands is formed from a different material than a second of said first plurality of twined electrically conductive strands.

18. A method according to claim 11, wherein:

said diameter of said first conductive cable is reduced at least approximately 24% relative to an overall cross sectional diameter of said first plurality of twined electrically conductive strands.

19. A method according to claim 11, wherein:

said diameter of said first conductive cable is reduced at least approximately 30% relative to an overall cross sectional diameter of said first plurality of twined electrically conductive strands.

* * * * *